(12) United States Patent
Lunnen et al.

(10) Patent No.: US 7,795,408 B2
(45) Date of Patent: Sep. 14, 2010

(54) **METHOD FOR CLONING AND EXPRESSION OF ACC65I RESTRICTION ENDONUCLEASE AND ACC65I METHYLASE IN *E. COLI***

(75) Inventors: Keith Lunnen, Essex, MA (US); John Greci, Manchester, MA (US); Geoffrey Wilson, South Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 11/818,298

(22) Filed: Jun. 14, 2007

(65) Prior Publication Data

US 2008/0009036 A1    Jan. 10, 2008

Related U.S. Application Data

(60) Provisional application No. 60/815,553, filed on Jun. 14, 2006.

(51) Int. Cl.
| | |
|---|---|
| *C07H 21/02* | (2006.01) |
| *C07H 21/04* | (2006.01) |
| *C12P 21/06* | (2006.01) |
| *C12N 1/20* | (2006.01) |
| *C12N 15/74* | (2006.01) |

(52) U.S. Cl. ............... 536/23.1; 435/471; 435/69.1; 435/252.3

(58) Field of Classification Search ............... None
See application file for complete search history.

(56) References Cited

U.S. PATENT DOCUMENTS

| 6,383,770 B1 | 5/2002 | Roberts et al. |
| 6,689,573 B1 | 2/2004 | Roberts et al. |
| 6,905,837 B2 | 6/2005 | Roberts et al. |

FOREIGN PATENT DOCUMENTS

WOWO-2007/097778-WO    8/2007

OTHER PUBLICATIONS

BLAST [online], 2008 [retrieved on Nov. 7, 2008]. Retrieved from the Internet:< URL: http://blast.ncbi.nlm.nih.gov/Blast.cgi>, pp. 1-6.*
Roberts and Macelis, *Nucl. Acids Res.*29:268-269 (2001).
REBASE®, <http://rebase.neb.com/rebase>.
Skoglund, *Gene*, 88(1): 1-5 (1990).

\* cited by examiner

*Primary Examiner*—Joanne Hama
(74) *Attorney, Agent, or Firm*—Harrier M. Strimpel

(57) ABSTRACT

An isolated DNA is provided which encodes a protein that is capable of binding to 5'GGTACC-3', the isolated DNA being capable of hybridizing to SEQ ID NO:3 under stringent hybridization conditions. The isolated DNA may be alternatively characterized as coding for a protein having an amino acid sequence comprising SEQ ID NO:5 or by an amino acid sequence with an expectation value of less than $E=e^{-02}$ in a BLAST search using SEQ ID NO:5. Vectors containing the isolated DNA and host cells expressing the vectors as well as a method for making recombinant Acc65I having the above properties are also provided.

4 Claims, 8 Drawing Sheets

Figure 1-1 (SEQ ID NO:1)

```
   1 GAATTCAAAA TTGGCGTAAT TGTAGCAGAT TTATAAAGGT TGTTTTCGCA
  51 TGTTAGAAAG TGAAAATGGT GTTCTAGTAT AGATATTATG AAAAAGAAAG
 101 AGTCGTAGTC CACTCTTTCT TTCTCTATTA ATTAGTTAGC ATTTATTAAT
 151 CTTTTATCCC AATCATCAAT TAATCCAATT GGTAAACCAT TAACACCTGA
 201 GGAACTAAAA CTGATTACCT GAACATCTTT AGAGTCAAGA TCAATATTTG
 251 GTGGAAGATC ATTATCAACC AAAATCATTT GACATAAAAT ATTTGCACTT
 301 TTGAATTTTT CAGCTAAATC AATTAACGCA TTAAATAGGT TTTTATATTT
 351 TTCTGGATCA GAGACACCTT CCTCAACATC TTCTCTGTTC TGATTAAAAT
 401 TAGGATTTTT ATAAGTTTTA CCAAGAAATT TACCTACCGT ATCGATCATT
 451 AATAAACCTG GTAAATTCGT CTCTTTTGAT AATTTTTGCT CGGCTTTGTT
 501 GCACAAAGAT TTAAAAACTA GGATTTCCCA TATCTACTCA AATTTAAGTG
 551 ACAACTCGGG TGTGAGGTCT GCCTAAATCG GTAAATCTAT TTAATACTGC
 601 CACTCGTGCA TGAATCTCAT TGACTTGACT TTGAAAGTTT CTCGCACTGA
 651 GTTTATCGCC TAATAACTTG ATGCAATGCA TCTTGGTTTC AACCAAACTT
 701 CGCCGATGAT AGCCTGACCA TTTCTTCCAA ATAGTTCTTC CTAAACGCTT
 751 AACTGTTCTA AGCAAGTCAT TGCGCTATAG CGAGCCCATC TTTTTATCTT
 801 TCCATGGCTT GGCATTTTTT CTGGGGGGAA TCACTGCATG TGCTTGCCGA
 851 TCTGCAATGA CCTGACGGCA TTGTTTTGTG TCATAAGCCC CGTCGGTATA
 901 GACTGAATCA ATCTGCTCAT CCAACGGGAT TGATCAAGT AAATCACCAA
 951 GTACCTGTGA ATCACTTACA TTGTTGGTCG TGAGCTGAAC TGCCCGTATT
1001 TGTAGGGTTT TAGCATCTAT ACCAATATGG AGTTACGCC ATTGGCGACG
1051 ATATTCAGGC TGATGTTTCT TACGTTTCCA TTCACCTTCA CCTAAAAACT
1101 TCAAGCCCGT GGAATCGACA AGTAGATGCA GTCCATTGCA ACTCTTCTCA
1151 TAGCTAATTT GAATATCAAT ATGCTTTGT CTTCTACAAA GCGTACTGTA
1201 ATCTGGTGCT GCCCAATTTA ATCCGCAAAG GTTAATCAGA CTTTGAACAA
1251 AACCTGTGAC CATGCGTAAA GACAATCGAA ATAGGGATTT GATCATCAGA
1301 CAGCACTGGA TGGCAGTATC AGAATAGGTT TGATTTCGAC CATGCTTGCC
1351 TTGTGATTGT GCGTACCACT GGGTCTTTGG ATCGAACCAA ATGGCAATAT
1401 TCCCACGATT AATGAGAGCT CGGTTATATG CGGGCCAATT GGTTGTGCGG
1451 TAGATTTTGT GTGTAGGCTT CTTCATTTGA AAATTATATC GCTGAAGAAG
1501 CCCTTAAGAA TAGCTTTGTG CAACAAAGCC GTTTTGGATT AATAAAGTAT
1551 TTTCAAGGTC AATTATAAGG TCATAGATTA TTCAAAGACT TCAAATTTAA
1601 ATTCATGATC TTTATTTTA ATATATTCAA GTCTAGCAAT CGAAACATCA
1651 ACTATTCTTT TATATCCAGC CTCATAGGCA ACATGATTAG TTGGTATTTG
1701 GTCTGAGGAT TCCATTAATA TACATTTTCG ATTTGCACCA TTCATTTTAT
1751 TTAATTCATA AATGGCGTGT GCTGTAGTAG CTGAACCTGC AAAAAAATCT
1801 AAAACTACTG CATTCTCTTC AGACATTGCA TCAATAATTT TTTTAATAAA
1851 TTCAATTGGC TTTGGTGTAT CAAATATCTT TTGACCAAAA ATACTTGTGA
1901 TTTCATTAGT TGCTCTTCA GTATAAAGAG ACGGATCATT CCATATAGTT
1951 CGAATCTTTT TCCTTTTTG ACCGTCCTCT TTCCCAGCAT AATTTTTAAC
2001 GTAAATTACG CCATTTTTAC TTGAATATAA TTGCCATACA CGTTCTCTCG
2051 TAGTTGTTTC TCCCCATAGC CATCTACGAT CAATTCCTTT CGAATCCTTT
2101 GGTAAAACTT TTCTCCAACC TTCACGAGGA TCAACCGAAA CTTCGCCTGT
2151 CTCAAGATTT GCATAAAGTG GAAAGGCCAT CAAAGGACGG TCGCTTTTCA
2201 GACTACCTTC TCCTTTTTTT CTAAATAACC CATCTATACG GTATTTTCCA
```

Figure 1-2 (SEQ ID NO:1)

```
2251 TAAGCATCTG CTTTATCATA AATCGTATCT TCGTCAGACT CTCCTCTTAA
2301 GGTAGCCTGA TTTGATTTAC CATATACAAG TAAATATTCA TGAGTAGATG
2351 CTAAGTTTTT TTTACTTCCT TTACCATTCT TGGAGCGGCA AACAACAATA
2401 TTGCCAATAA AGTTTTTTTC TCCAAAAACT CTATCCATTA CTATTTTTAA
2451 ATATGGAAAT TCATAATCAT CAATACTAAC TGCAATAACT CCACTGTCCT
2501 TTAATAGTTC ACGAGCTGTT ACTAACCGTG GAAGCATAAA TTCAACCCAT
2551 GCTTCATGAG ATCCCAGTAA ACCGATTTCA GGCGATTTTC TATTATCAGG
2601 ATAGATAAAA TTTGATCCTG TATTATAAGG TGGATCTATA TAACACAAAT
2651 CAATAATCTC AGGACCGTTC AGGAGTAATT TCCTTAAGGA AATTAAGTTA
2701 TCTCCACTAT AAATAACAGC ATCAGTTTGC TCCCAATTTC TTGATAAATT
2751 AGAATTAGTT TTAACATCAT TAGTTACAAA GTCAAAGAG CTAGCGTGGG
2801 AGAACTCTTG TTGTAACTTA CGGATTTTAG ACTCAATTAC TGATAGCATG
2851 TCAGCTCCTA CTTGGACCAA CATTATAACT GAGCCTGCTC AAGAGAAGGA
2901 ATGTAATGAA ATTAAATGCT GAGAATTTAA GTATTCAGGA CAATTAGCA
2951 GAATTTGATC AATGGCTCAC AGCTAGACTA GATAAAATCA AAGATTCAGA
3001 AAAATTCAAT TCAGAAATTA ACTCCCTCTG TAATTGTATT ACCGTATTAT
3051 CTCCTCTTTT AGAAAACTTC AGTGATCCTT CCACCTGTAC AATTCATAGC
3101 TTAGTGAATG CGGTTATAGA AGCCAGCAAT AGAATAGTCT CTGGTAGTAG
3151 TTTTGGAGGT GATGAAGCTG CTCTCAACAA CTTTTATGAG TCTTTTTTTA
3201 ACTTGCTATT CCTAACCAGT GGGGCAACAG ATAACAACCT AAAGAATCAT
3251 TTTCTAATTA AACTTAATGA AGACGATATT ACACCTCTCA TACCTAAACG
3301 TGGTTCAATA AAGAAACAGA TCACATTCAA ACTTTATGAA ATTCCTACAA
3351 CTACTAAATC TGACTTTATC GCTCGTACCT TAGCAAGTTG TTTTACAGGA
3401 ACTAAATATC CCCTCCTAGT AAAGACAGAA CCATTTTTCG ATCTTGAAAC
3451 ATACTTTAAA ATTTTTTTAG AAGAATACAT TAAGCTTATT CTTGATGATG
3501 AAGAAGATTT ATTACAACTC TGGGCTATCT GCCACTCATT TGTTGAATTA
3551 TCCACTAACC CTCATGGTTC CAATTTGGGT AAATATTTAT TAAATTCTTG
3601 TACGATTTTT AAAGTTAGAG GTAGTGTATC AGCATCAGGT GGTCACGTTA
3651 CTGAATCTAT ACTTAGGGAA AAGTTATCAA ACATCGGGTT AAGAGCTGAT
3701 ATTGATTACA ATAATAATGA TGTCAAAATT GGTGATGATG AAATTATTGA
3751 AGACGGGAAA AGAAAAAAGA AAACTCGTGC GTATGACTTT ATAATTCCTT
3801 ATAAAATAGA TAACTGGGAA CCAAAACCTA AGCTATTTAT CCAATCACAA
3851 TTTTACGCTG GGGATTCTGG CAGTGTATCT CATAAAGTCG TAGATCAAAC
3901 TCAAAGTTCA AGAGTATTTA CACTAACCAA ATATCCGAAT GCTAAATTTG
3951 TTGAATATTT AGATGGTGCT GGTTACTACG CTTCTTTAAG AGGTGATTTA
4001 CAGCACATGC TATCTTTCAG CAATACAGAA TCTTTTTTTC AAGTAAAAAG
4051 TATTCTTTTA CGTTTAAGAC GTGAATTCCA AAAGATCGAT TTTTTAACAG
4101 CTATTGAAAT TCAGCATGCT GTACTAATCA GCAAATCTCG GACTCATAAA
4151 GATCTCCAAA ATCTTCTTAT AAAAGATAAC TATTCTATCC AAGAAATAGA
4201 AAGAGCTATT CAAACCAATT TAGAACTAGG TCTTATTACT AAAAATGAAT
4251 CAGATGAAAT TGTAATACCT ACAGAACATA TTTGTATCGC CCGGAGACTT
4301 TTAATTTTAG ATATTGCTGC AAACTATTCA TGCTCTATTA CTCAGGCAGA
4351 AAAGTCTAGC CAAAAATATT TATTAGTACC GGGCAATGGG GCCAATAAAG
4401 GAATTAAGGA GTCAAGCTA GCTGAGTTAG CTTTTGACTT ATGTAAAGAT
4451 ATTAATATAA CACCGACTGA ATTATTGAA GACATCGAAT GGCTCTTAGA
4501 TGAGGGAGTA ATTAAACGAT TTAGTATCA ATGGCTGAGC AAGAGCTCAG
4551 CCATATTTTT CATTTAATCT AAGCTAAAAT ATTTATTCAT TATTCTTGTT
4601 CTCAATAAAA TAGCACTATT AGAAATTTGG TTATTTTTAT ACGGATTAAG
```

Figure 1-3 (SEQ ID NO:1)

```
4651 CAAAACTCAA TATTATAAAA TCATTAACTT ATTTCCCCTC ATAAGCCAAT
4701 AATATTATTT TAAATTTCCA TAGAAAAATC TAMAAATAAT GACATAACCT
4751 GTCCATACAT CACTACATTA TCTACTTTAT AAAACAAGAA TATCAACTTG
4801 TTAAATTTAG GGGCAGAAGA GTGAAAGGTA TAATTCTTGA TTTTTCAATT
4851 CAGACCAATA GTGGAATTAT TTCAGGGGAA GATCAAAAAC GCTATTCATT
4901 TATAGGTAGC GAATGGAAGG AAAGTTCTCC ACCTCAACGT GGTCTTAAGA
4951 TAGACTTTGA TCTTGACACA ACAGGACAAG CAATCGGTGT ATATCAAGCA
5001 CTAGATAATT CTATCAGATC AAACGCTCAC ATAACTAATA GTACCGAAAA
5051 ATCAGAAGAA GATTATAATA TTTTTGATTG GTTTATTAAG TGTTTAAAGA
5101 ATTATGCAAA TTTTAATGGT CGTGCTAGAC GTAAGGAATT CTGGTTCTTT
5151 TATCTCGCAT TAGTAATTTG CAATATTTTT GCGATGGTCT TAGATGCAAT
5201 TTTAGAAACT GAAGTTATTT TTTATGGAAT AGTTACTTTA GCAACTATTA
5251 TTCCTTTTCT TGCTGTTTCT GCTCGCCGAC TACATGACAT AGGAAAATCG
5301 GGCTGGTGGT ATCTTATTAG TCTAACTATT ATAGGTATTA TTCTACTAAT
5351 TATCTGGTGG GCAAAAGAAG GAGAAGCCTT TAGTAATCCA TATGGTGATA
5401 TAGCGAAATA AAAAATAGAC CCTCTCAATC TGAGAGGGTC TATTTTTTAA
5451 TATAAGGACT TATTAAAATA TATTTTAAAG ATCCTGAATA ATAAATCTAA
5501 TCTCAACTCG TCGATTATTT GCTGCATTCG GATTATCTTT ATTTAATAAT
5551 CTATCAGGAC CATAACCTAC GACTGAAATT CTTTGAACCA ATTCAGAAGA
5601 CTGAAGCTGG GTAAACAATG CTTTTCTAGC TTCTCTTGCT CTGCCAGCTG
5651 ATAAAGTATA ATTATCATCA AATGGTGAAC ACACTTGAGA AATATTTGAT
5701 TTAACACCAT TTACTGGTGC TGCATCTGTG TGTCCTTCAA TCTGTATATT
5751 CAGCAATCGA TTATCAATCA TATTTTTTTG GATTAATGGA GCCAACCTTT
5801 CCTTGAAAGC TT
```

Figure 2a (SEQ ID NO:2)

```
   1 ATGTTGGTCC AAGTAGGAGC TGACATGCTA TCAGTAATTG AGTCTAAAAT
  51 CCGTAAGTTA CAACAAGAGT TCTCCCACGC TAGCTCTTTT GACTTTGTAA
 101 CTAATGATGT TAAAACTAAT TCTAATTTAT CAAGAAATTG GGAGCAAACT
 151 GATGCTGTTA TTTATAGTGG AGATAACTTA ATTTCCTTAA GGAAATTACT
 201 CCTGAACGGT CCTGAGATTA TTGATTTGTG TTATATAGAT CCACCTTATA
 251 ATACAGGATC AAATTTTATC TATCCTGATA ATAGAAAATC GCCTGAAATC
 301 GGTTTACTGG GATCTCATGA AGCATGGGTT GAATTTATGC TTCCACGGTT
 351 AGTAACAGCT CGTGAACTAT TAAAGGACAG TGGAGTTATT GCAGTTAGTA
 401 TTGATGATTA TGAATTTCCA TATTTAAAAA TAGTAATGGA TAGAGTTTTT
 451 GGAGAAAAAA ACTTTATTGG CAATATTGTT GTTTGCCGCT CCAAGAATGG
 501 TAAAGGAAGT AAAAAAAACT TAGCATCTAC TCATGAATAT TTACTTGTAT
 551 ATGGTAAATC AAATCAGGCT ACCTTAAGAG GAGAGTCTGA CGAAGATACG
 601 ATTTATGATA AAGCAGATGC TTATGGAAAA TACCGTATAG ATGGGTTATT
 651 TAGAAAAAAA GGAGAAGGTA GTCTGAAAAG CGACCGTCCT TTGATGGCCT
 701 TTCCACTTTA TGCAAATCTT GAGACAGGCG AAGTTTCGGT TGATCCTCGT
 751 GAAGGTTGGA GAAAAGTTTT ACCAAAGGAT TCGAAAGGAA TTGATCGTAG
 801 ATGGCTATGG GGAGAAACAA CTACGAGAGA ACGTGTATGG CAATTATATT
 851 CAAGTAAAAA TGGCGTAATT TACGTTAAAA ATTATGCTGG GAAAGAGGAC
 901 GGTCAAAAAA GGAAAAAGAT TCGAACTATA TGGAATGATC CGTCTCTTTA
 951 TACTGAAAGA GCAACTAATG AAATCACAAG TATTTTTGGT CAAAAGATAT
1001 TTGATACACC AAAGCCAATT GAATTTATTA AAAAAATTAT TGATGCAATG
1051 TCTGAAGAGA ATGCAGTAGT TTTAGATTTT TTTGCAGGTT CAGCTACTAC
1101 AGCACACGCC ATTTATGAAT TAAATAAAAT GAATGGTGCA AATCGAAAAT
1151 GTATATTAAT GGAATCCTCA GACCAAATAC CAACTAATCA TGTTGCCTAT
1201 GAGGCTGGAT ATAAAGAAT AGTTGATGTT TCGATTGCTA GACTTGAATA
1251 TATTAAAAAT AAAGATCATG AATTTAAATT TGAAGTCTTT GAATAA
```

Figure 2b (SEQ ID NO:3)

```
   1 ATGAAATTAA ATGCTGAGAA TTTAAGTATT CAGGAACAAT TAGCAGAATT
  51 TGATCAATGG CTCACAGCTA GACTAGATAA AATCAAAGAT TCAGAAAAAT
 101 TCAATTCAGA AATTAACTCC CTCTGTAATT GTATTACCGT ATTATCTCCT
 151 CTTTTAGAAA ACTTCAGTGA TCCTTCCACC TGTACAATTC ATAGCTTAGT
 201 GAATGCGGTT ATAGAAGCCA GCAATAGAAT AGTCTCTGGT AGTAGTTTTG
 251 GAGGTGATGA AGCTGCTCTC AACAACTTTT ATGAGTCTTT TTTTAACTTG
 301 CTATTCCTAA CCAGTGGGGC AACAGATAAC AACCTAAAGA ATCATTTTCT
 351 AATTAAACTT AATGAAGACG ATATTACACC TCTCATACCT AAACGTGGTT
 401 CAATAAAGAA ACAGATCACA TTCAAACTTT ATGAAATTCC TACAACTACT
 451 AAATCTGACT TTATCGCTCG TACCTTAGCA AGTTGTTTTA CAGGAACTAA
 501 ATATCCCCTC CTAGTAAAGA CAGAACCATT TTTCGATCTT GAAACATACT
 551 TTAAAATTTT TTTAGAAGAA TACATTAAGC TTATTCTTGA TGATGAAGAA
 601 GATTTATTAC AACTCTGGGC TATCTGCCAC TCATTTGTTG AATTATCCAC
 651 TAACCCTCAT GGTTCCAATT TGGGTAAATA TTTATTAAAT TCTTGTACGA
 701 TTTTTAAAGT TAGAGGTAGT GTATCAGCAT CAGGTGGTCA CGTTACTGAA
 751 TCTATACTTA GGGAAAAGTT ATCAAACATC GGGTTAAGAG CTGATATTGA
 801 TTACAATAAT AATGATGTCA AAATTGGTGA TGATGAAATT ATTGAAGACG
 851 GGAAAAGAAA AAAGAAAACT CGTGCGTATG ACTTTATAAT TCCTTATAAA
 901 ATAGATAACT GGGAACCAAA ACCTAAGCTA TTTATCCAAT CACAATTTTA
 951 CGCTGGGGAT TCTGGCAGTG TATCTCATAA AGTCGTAGAT CAAACTCAAA
1001 GTTCAAGAGT ATTTACACTA ACCAAATATC CGAATGCTAA ATTTGTTGAA
1051 TATTTAGATG GTGCTGGTTA CTACGCTTCT TTAAGAGGTG ATTTACAGCA
1101 CATGCTATCT TTCAGCAATA CAGAATCTTT TTTTCAAGTA AAAAGTATTC
1151 TTTTACGTTT AAGACGTGAA TTCCAAAAGA TCGATTTTTT AACAGCTATT
1201 GAAATTCAGC ATGCTGTACT AATCAGCAAA TCTCGGACTC ATAAAGATCT
1251 CCAAAATCTT CTTATAAAAG ATAACTATTC TATCCAAGAA ATAGAAAGAG
1301 CTATTCAAAC CAATTTAGAA CTAGGTCTTA TTACTAAAAA TGAATCAGAT
1351 GAAATTGTAA TACCTACAGA ACATATTTGT ATCGCCCGGA GACTTTTAAT
1401 TTTAGATATT GCTGCAAACT ATTCATGCTC TATTACTCAG GCAGAAAAGT
1451 CTAGCCAAAA ATATTTATTA GTACCGGGCA ATGGGGCCAA TAAAGGAATT
1501 AAGGAGTCTA AGCTAGCTGA GTTAGCTTTT GACTTATGTA AAGATATTAA
1551 TATAACACCG ACTGAATTTA TTGAAGACAT CGAATGGCTC TTAGATGAGG
1601 GAGTAATTAA ACGATTTTAG
```

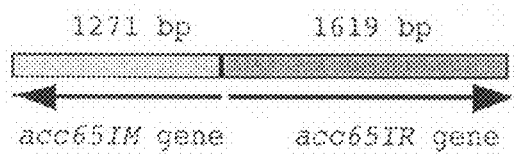

Figure 3a. Organization of genes for the Acc65I restriction-modification system

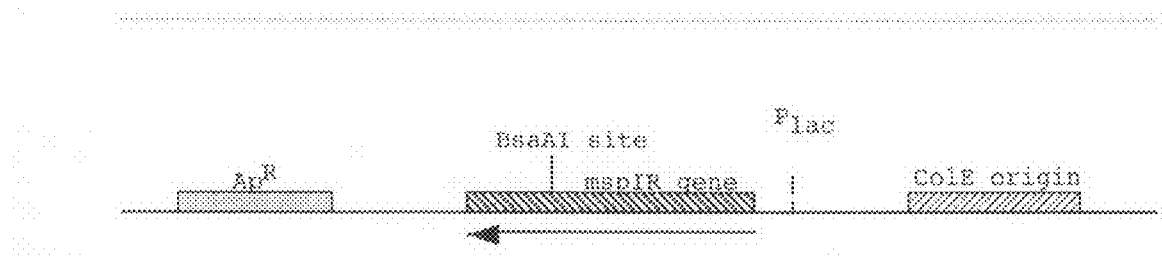

Figure 3b. pCAB16 vector for insertion of Acc65IM gene at BsaAI site

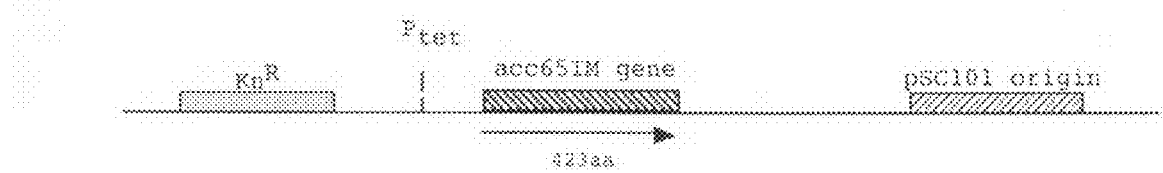

Figure 3c. Organization of the plasmid clone, pSX20-acc65IM #4 carrying the acc65IM gene inserted into the BamHI site of pSX20

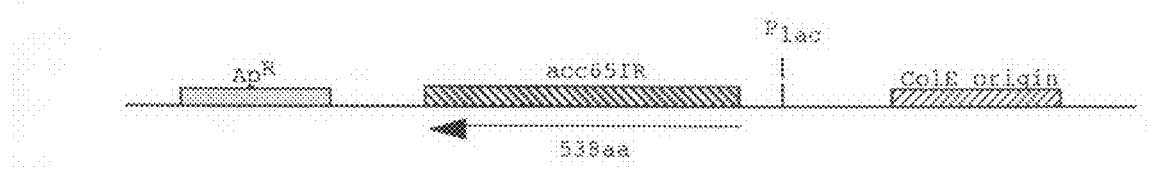

Figure 3d. Organization of the plasmid clone, pRRS-acc65IR #6, carrying the Acc65IR gene inserted into the XbaI/XmaI site of pRRS Figure 4a (SEQ ID NO:4)

```
  1 mLVQVGADML SVIESKIRKL QQEFSHASSF DFVTNDVKTN SNLSRNWEQT
 51 DAVIYSGDNL ISLRKLLLNG PEIIDLCYID PPYNTGSNFI YPDNRKSPEI
101 GLLGSHEAWV EFMLPRLVTA RELLKDSGVI AVSIDDYEFP YLKIVMDRVF
151 GEKNFIGNIV VCRSKNGKGS KKNLASTHEY LLVYGKSNQA TLRGESDEDT
201 IYDKADAYGK YRIDGLFRKK GEGSLKSDRP LMAFPLYANL ETGEVSVDPR
251 EGWRKVLPKD SKGIDRRWLW GETTTRERVW QLYSSKNGVI YVKNYAGKED
301 GQKRKKIRTI WNDPSLYTER ATNEITSIFG QKIFDTPKPI EFIKKIIDAM
351 SEENAVVLDF FAGSATTAHA IYELNKMNGA NRKCILMESS DQIPTNHVAY
401 EAGYKRIVDV SIARLEYIKN KDHEFKFEVF E
```

Figure 4b (SEQ ID NO:5)

```
  1 mKLNAENLSI QEQLAEFDQW LTARLDKIKD SEKFNSEINS LCNCITVLSP
 51 LLENFSDPST CTIHSLVNAV IEASNRIVSG SSFGGDEAAL NNFYESFFNL
101 LFLTSGATDN NLKNHFLIKL NEDDITPLIP KRGSIKKQIT FKLYEIPTTT
151 KSDFIARTLA SCFTGTKYPL LVKTEPFFDL ETYFKIFLEE YIKLILDDEE
201 DLLQLWAICH SFVELSTNPH GSNLGKYLLN SCTIFKVRGS VSASGGHVTE
251 SILREKLSNI GLRADIDYNN NDVKIGDDEI IEDGKRKKKT RAYDFIIPYK
301 IDNWEPKPKL FIQSQFYAGD SGSVSHKVVD QTQSSRVFTL TKYPNAKFVE
351 YLDGAGYYAS LRGDLQHMLS FSNTESFFQV KSILLRLRRE FQKIDFLTAI
401 EIQHAVLISK SRTHKDLQNL LIKDNYSIQE IERAIQTNLE LGLITKNESD
451 EIVIPTEHIC IARRLLILDI AANYSCSITQ AEKSSQKYLL VPGNGANKGI
501 KESKLAELAF DLCKDINITP TEFIEDIEWL LDEGVIKRF
```

METHOD FOR CLONING AND EXPRESSION OF ACC65I RESTRICTION ENDONUCLEASE AND ACC65I METHYLASE IN E. COLI

RELATED APPLICATIONS

This application claims priority to U.S. provisional application Ser. No. 60/815,553 filed Jun. 14, 2006.

BACKGROUND OF THE INVENTION

Present embodiments of the invention relate to a Type II restriction endonuclease, *Acinetobacter calcoaceticus* 65 (Acc65I), obtainable from the recombinant strain carrying the genes for the Acc65I restriction-modification system from Acc65I in *E. coli*, and to a process for producing the same.

Restriction endonucleases are enzymes that occur naturally in certain unicellular microbes—mainly bacteria and archaea—and that function to protect these organisms from infections by viruses and other detrimental DNA elements. Restriction endonucleases bind to specific nucleotide (nt) sequences in double-stranded DNA molecules (dsDNA) and cleave the DNA molecules, often within or close to these sequences, fragmenting the molecules and triggering their ultimate destruction. Restriction endonucleases commonly occur with one or more companion enzymes termed modification methyltransferases. The methyltransferases bind to the same nt sequence in dsDNA as the restriction endonuclease, but instead of cleaving the DNA, they modify it by the addition of a methyl group to one of the bases in each strand of the sequence. This modification prevents the restriction endonuclease from binding to that site thereafter, effectively rendering the site resistant to cleavage. Methyltransferases act as cellular antidotes to the restriction endonucleases they accompany, protecting the DNA of the cell from destruction by its own restriction endonucleases. Together, a restriction endonuclease and its companion modification methyltransferase(s) form a restriction-modification (R-M) system, an enzymatic partnership that accomplishes for microbes, to some extent, what the immune system accomplishes for multicellular organisms.

A large and varied group of restriction endonucleases termed 'type II' cleave DNA at defined positions, and can be used in the laboratory to cut DNA molecules into precise fragments for gene cloning and analysis. The biochemical precision of type II restriction endonucleases far exceeds anything achievable by chemical methods, and so these enzymes have become the reagents sine qua non of modern molecular biology. They are the 'scissors' by means of which genetic engineering and analysis is performed, and their adoption has profoundly impacted the biomedical sciences over the past 25 years, transforming the academic and commercial arenas, alike. Their utility has spurred a continuous search for new restriction endonucleases, and a large number have been found. Today more than 200 Type II endonucleases are known, each possessing different DNA cleavage characteristics (Roberts and Macelis, *Nucl. Acids Res.* 29:268-269 (2001)); (REBASE®, http://rebase.neb.com/rebase). Concomitantly, the production and purification of these enzymes have been improved by the cloning and over-expression of the genes that encode them in non-natural production strain host cells such as *E. coli*.

Since the various restriction enzymes perform similar roles in nature, and do so in much the same ways, it might be thought that they would resemble one another closely in amino acid sequence, organization, and behavior. Experience shows this not to be true, however. Surprisingly, far from resembling one another, most Type II restriction enzymes appear unique, resembling neither other restriction enzymes nor any other known kind of protein. Type II restriction endonucleases seem to have arisen independently of one another for the most part during evolution, and to have done so hundreds of times, so that today's enzymes represent a motley collection rather than a discrete family. Some restriction endonucleases act as homodimers, some as monomers, others heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. Often the methyltransferase is separate from, and functions independently of, the restriction endonuclease, but sometimes the two are fused and interdependent. When two methyltransferases are present, on some occasions they are separate proteins, on others they are fused. The orders and orientations of restriction and modification genes vary, with all possible organizations occurring. Several kinds of methyltransferases exist, some methylating adenines (m6A-MMases), others methylating cytosines at the N-4 position (m4C-MMases), or at the 5 position (m5C-MMases). Usually there is no way of predicting, a priori, which modifications will block a particular restriction endonuclease, which kind(s) of methyltransferases(s) will accompany that restriction endonuclease in any specific instance, nor what their gene orders or orientations will be.

From the point of view of cloning a Type II restriction endonuclease, the great variability that exists among restriction-modification systems means that, for experimental purposes, each is unique. Each enzyme is unique in amino acid sequence and catalytic behavior; each occurs in unique enzymatic association, adapted to unique microbial circumstances; and each presents the experimenter with a unique challenge. Sometimes a restriction endonuclease can be cloned and over-expressed in a straightforward manner but more often than not it cannot, and what works well for one enzyme can work not at all for the next. Success with one is no guarantee of success with another.

There is a continuing need for novel type II restriction endonucleases. Although type II restriction endonucleases that recognize a number of specific nucleotide sequences are currently available, new restriction endonucleases that recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In an embodiment of the invention, an isolated DNA coding for an endonuclease capable of binding 5'G/GTACC-3' in a DNA substrate is provided which is characterized by SEQ ID NO:3, or by a DNA capable of hybridizing to SEQ ID NO: 3 under stringent hybridization conditions.

An example of the endonuclease is Acc65I restriction endonuclease that cleaves dsDNA between G and G as indicated below, producing DNA fragments with 4-nt cohesive ends.

```
5' G/GTACC-3'

3'-CCATG/G-5'
```

An example of stringent hybridization conditions include 0.75M NaCl, 0.15 Tris, 10 mM EDTA, 0.1% Sodium Pyrophosphate, 0.1% SLS, 0.03% BSA, 0.03% Ficoll 400, 0.03% PVP and 100 µg/ml boiled calf thymus DNA at 50° C. for about 12 hours and washing 3 times for 30 minutes with 0.1×SET, 0.1% SDS, 0.1% sodium pyrophosphate and 0.1M phosphate buffer at 37° C.-55° C.

In another embodiment of the invention, an isolated protein is provided that encodes a protein comprising SEQ ID NO:5 or having an amino acid sequence identified by an expectation value of less than $E=e^{-02}$ in a BLAST search using SEQ ID NO:5.

In another embodiment of the invention, a cloning vector is provided that includes the DNA described above and a host cell transformed by such cloning vector.

In another embodiment of the invention, a method is provided for producing recombinant Acc65I restriction endonuclease by culturing a host cell transformed with the vector described above under conditions suitable for expression of the endonuclease.

BRIEF DESCRIPTION OF THE FIGURES

FIG. 1. Cloned DBA sequence (SEQ ID NO:1) expressing Acc65I, the DNA derived from *Acinetobacter calcoaceticus* 65.

FIG. 2. Nucleotide sequences of a) the Acc65IM gene (SEQ ID NO:2), and b) the Acc65IR gene (SEQ ID NO:3).

FIG. 3. Gene organization of a) the Acc65I restriction-modification system, b) the plasmid clone pCAB16-Acc65IM #5 carrying the Acc65I methyltransferase gene inserted into the BsaAI site of pCAB16, c) the plasmid clone pSX20-Acc65IM #4 (pSX20, a pBR322 derivative containing kanamycin marker) carrying the Acc65I methyltransferase gene inserted into the BamHI site of pSX20, and d) the plasmid clone pRRS-Acc65IR #6 carrying the Acc65I endonuclease gene inserted into the XbaI/XmaI site of pRRS (Skoglund et al. *Gene* 88(1):1-5 (1990).

FIG. 4. Predicted amino acid sequences of a) the M-Acc65I methyltransferase, and b) the R-Acc65I endonuclease.

DETAILED DESCRIPTION OF THE INVENTION

Figure 5:
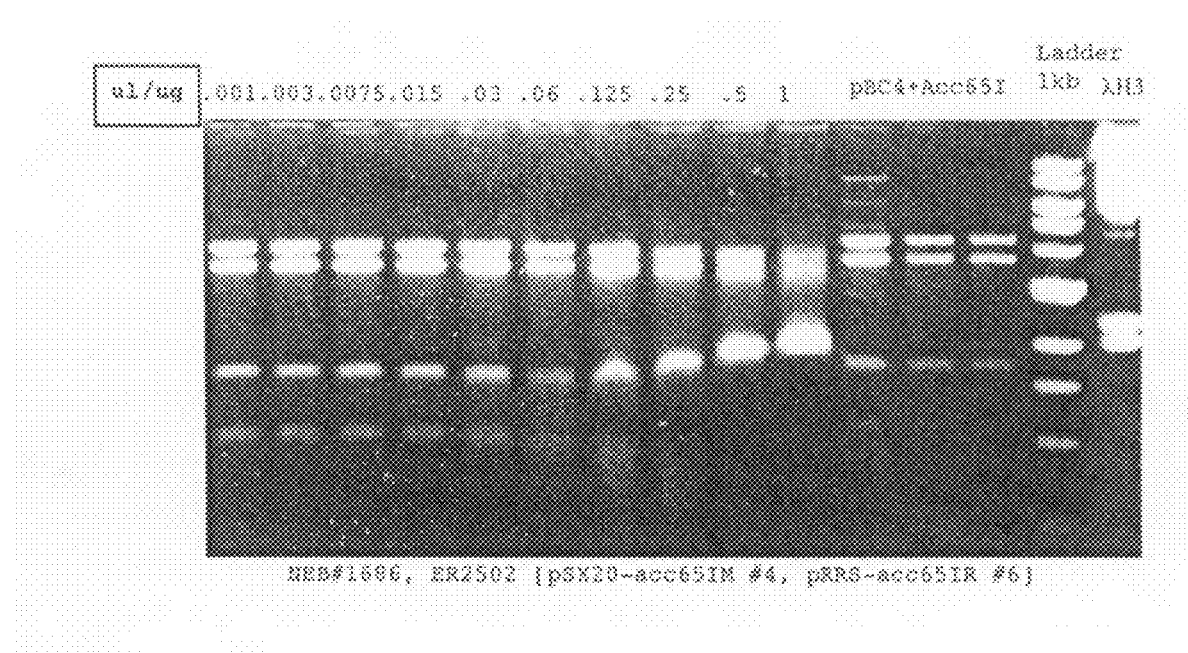
FIG. 5. Restriction assay of NEB Strain #1686 *E. coli* ER2502 [pSX20-acc65IM #4, pRRS-acc65IR #6] (New England Biolabs, Inc. (NEB), Ipswich, Mass.).

In embodiments of the invention, Acc65I is obtained by culturing transformed *E. coli* host cells, and recovering the endonuclease from the cells.

For recovering the enzyme of the present invention, *E. coli* may be grown using any suitable culturing technique. For example, *E. coli* may be grown in Luria broth media (BBL Microbiology Systems, Cockeysville, Md.) supplemented with 100 µg/ml ampicillin, 50 µg/ml kanamycin incubated aerobically at 37° C. Cells in the late logarithmic stage of growth are collected by centrifugation and either disrupted immediately or stored frozen at −70° C.

The Acc65I endonuclease can be isolated from bacterial host by conventional protein purification techniques. For example, cell paste is suspended in a buffer solution and ruptured by sonication, high-pressure dispersion or enzymatic digestion to allow extraction of the endonuclease by the buffer solution. Intact cells and cellular debris are then removed by centrifugation to produce a cell-free extract containing Acc65I. The Acc65I endonuclease is then purified from the cell-free extract by ion-exchange chromatography, affinity chromatography, molecular sieve chromatography, or a combination of these methods to produce the endonuclease of the present invention.

The details of cloning and expression of Acc65I is provided in the Examples. Alternatively, any person of ordinary skill in the art may generate the DNA sequences in FIG. 2 encoding the restriction endonuclease or methylase by commercial DNA synthesis technology or by PCR amplification using primers derived from the sequences in FIG. 2 and may additionally clone the synthesized DNA into a vector for expression in a competent host or by in vitro transcription/translation systems (U.S. Pat. Nos. 6,689,573; 6,905,837, 6,383,770).

The sequence for Acc65I methylase and restriction endonuclease are provided in FIG. 2. While Acc65IR has low homology to other restriction genes, variants of Acc65I are anticipated that retain Acc restriction activity and are intended to be included within the scope of the invention. For example, any DNA sequence encoding a protein having an amino acid sequence which matches the amino acid sequence of Acc65I in a blast search using an expectation value of less than $E=e^{-02}$ is embodied in the invention (see international application PCT/US06/30419, incorporated herein by reference).

The cleavage characteristics of the Acc65I restriction endonuclease and its variants differ in an important way from those of isoschizomers such as KpnI. Acc65I cleaves DNA to produce fragments with 5'-extensions. KpnI, in contrast, cleaves to produce fragments with 3'-extensions. 5'-extensions are advantageous in that they can be filled-in by DNA polymerase to produce flush-ended fragments whose termini retain five of the six bases that comprise the Acc65I recognition sequence, that is to say 5'-GGTACC. If these filled-in fragments are ligated to other flush-ended fragments that bear a cytosine at their 5'-terminus, the Acc65I site, 5'-GGTACC, is restored at the junction. The ligated fragments can thus be re-cleaved with Acc65I; the site is not lost in the joining process. Furthermore, ligating filled-in Acc65I sites to one another produces a new sequence at the junction: 5'-GGTACGTACC (SEQ ID NO:6). This new sequence can no longer be cleaved by Acc65I (i.e., the Acc65I site is lost) but it can be cleaved by another restriction endonuclease, SnaBI, which recognizes the central 5'-TACGTA of the composite sequence. Finally, the termini of the DNA fragments produced by Acc65I are identical in sequence and polarity to those produced by several other restriction enzymes including BsiWI (recognition sequence: 5'-C/GTACG), BsrGI (recognition sequence 5'-T/GTACA), and TatI (recognition sequence 5'-W/GTACW). Consequently, DNA fragments produced by Acc65I will naturally anneal to and ligate with those produced by BsiWI, BsrGI and TatI.

Present embodiments of the invention are further illustrated by the following Examples. These Examples are provided to aid in the understanding of the invention and are not construed as a limitation thereof.

The references cited above and below are herein incorporated by reference.

EXAMPLE I

Cloning of the Acc65I Restriction-Modification Genes

1. Preparation of Genomic DNA

Genomic DNA was prepared from 10 g of *Acinetobacter calcoaceticus* 65, by the following steps:
   a. Cell wall digestion by addition of lysozyme (2 mg/ml final), sucrose (1% final), and 50 mM Tris-HCl, pH 8.0.
   b. Cell lysis by addition of 24 ml of Lysis mixture: 50 mM Tris-HCl pH 8.0, 62.5 mM EDTA, 1% Triton.
   c. Removal of proteins by phenol-CHCl$_3$ extraction of DNA 2 times (equal volume).

d. Dialysis in 4 liters of TE buffer, buffer change four times.
e. RNase A treatment to remove RNA.
f. Genomic DNA precipitation in 0.4M NaCl and 0.55 volume of 100% isopropanol, spooled, dried and resuspended in TE buffer.

2. Genomic DNA Digestion and Library Construction

Restriction enzymes ApoI, BglII, EcoRI, HindIII and Sau3AI were used to individually digest ~10 microgram quantities of *Acinetobacter calcoaceticus* 65 genomic DNA to achieve complete and partial digestions. Following heat-inactivation of the restriction enzymes at 65° C. for 15 minutes, the ApoI-digests were ligated to EcoRI-cleaved, bacterial alkaline phosphatase (BAP)-dephosphorylated pUC19 vector, the BglII-, and Sau3AI-digests were ligated to BamHI-cleaved, BAP-dephosphorylated pUC19, and HindIII-digests were ligated to HindIII-cleaved, BAP-dephosphorylated pUC19. The ligations, performed overnight with T4 DNA ligase, were then used to transform the endA⁻ *E. coli* host, made competent by the CaCl₂ method. Several thousand Ampicillin-resistant (Ap$^R$) transformants were obtained from each ligation. The colonies from each ligation were pooled and amplified in 500 ml LB+Ap overnight, and plasmid DNA was prepared from them by CsCl gradient purification to make primary plasmid libraries.

3. Cloning the Acc65I Genes by Methylase-Selection

One microgram of each of the primary plasmid libraries was challenged by digestion with ~25 units of Acc65I at 37° C. for 1 hr. One half microgram of each of the Acc65I-digested primary plasmid libraries was challenged by digestion with ~5 units of lambda exonuclease at 37° C. for 30 min. followed by a heat inactivation at 65° C. for 15 min. The digestions were transformed back into *E. coli* and plated for survivors. 7 Ap$^R$ survivors arose from the BglII-library, and 37, 12, 10, and 11 from the HindIII-, Sau3AI-, EcoRI-, and ApoI-libraries, respectively. Plasmids from BglII, HindIII, Sau3AI, EcoRI, and ApoI survivors were extracted using mini-preps, and subjected to Acc65I-digestion. 3 of the 10 clones from the EcoRI-library were found to be resistant to Acc65I, but all those from BglII-, HindIII-, Sau3AI-, and ApoI-libraries were found to be sensitive. Plasmid DNA from survivors from the EcoRI-library was prepared by CsCl gradient purification. The individual clones from the EcoRI-library were inoculated into 50 ml LB+Ap$^R$ and grown at 37° C. overnight. All EcoRI-library clones did not express detectable Acc65I endonuclease activity.

4. Identification of the Acc65IRM Restriction-Modification Genes

The nucleotide sequence of the inserted DNA in the Acc65I-resistant plasmid clones from the EcoRI-library was determined by dideoxy-automated sequencing. Transposon-insertion into clone EcoRI using the NEB's GPS-1 System (Ipswich, Mass.), provided the initial substrates for sequencing. Inverse PCR, and primer-walking was used subsequently, on clones EcoRI, and inverse-PCR generated clones of *Acinetobacter calcoaceticus* 65 genomic DNA, to finalize the sequence. A total of 5812 bp was determined (FIG. 1), within which two complete open reading frames (ORFs) of 1271 bp (complement nt 1578-2849), and 1619 bp (nt 2906-4525) were found (FIG. 2). The two ORFs have diverging orientation and are separated by 32 bp (FIG. 3). Analysis of the ORFs indicated that the smaller ORF, subsequently termed Acc65IM, encodes the modification enzyme, M-Acc65I, and the larger ORF, subsequently termed Acc65IR, the R-Acc65I restriction enzyme. M-Acc65I is predicated to be 422 aa in length and to have a molecular mass of 48,398 Daltons (or 422 aa and 48,267 Daltons, without the N-terminal fMet). R-Acc65I is predicted to be 539 aa in length and to have a molecular mass of 61,221 Daltons (539 aa and 61,221 Daltons without the fMet) (FIG. 4).

The RM-Acc65I restriction-modification system appears to comprise a separate DNA-restriction gene (Acc65IR) and a DNA-methylation gene (Acc65IM). M-Acc65I includes amino acid sequence motifs characteristic of the beta-class of DNA-adenine methyltransferases including . . . DPPY . . . (aa 80-83), . . . VLDFFAGSATT . . . (SEQ ID NO:7) (aa 357-367). M-Acc65I displays substantial homology to the KpnI modification enzyme, and to several similar putative M-subunits in Genbank.

R-Acc65I shows little homology to any other protein in Genbank. This is typical of restriction endonucleases of type II R-M systems.

EXAMPLE II

Cloning of Acc65I Methylase and Endonuclease in *E. coli*

The Acc65IM gene was amplified by PCR from genomic DNA. Following purification, the resulting PCR fragment was blunt-end ligated into the BsaAI site of pCAB16, and transformed into *E. coli*. pCAB16 is a pUC18 derivative containing the mspIR gene in the polylinker of pUC18 in line with the Plac promoter. pCAB16 contains a single BsaAI site within the mspIR gene. Insertions at this site interrupt mspIR expression (which would otherwise be lethal) enabling plasmids containing inserts to be selectively recovered with high efficiency. Plasmid DNA of pCAB16-Acc65IM #5 containing the Acc65IM PCR insert was prepared by CsCl gradient purification (FIG. 3). The Acc65IM gene was purified from a BamHI-digested pCAB16-Acc65IM plasmid by gel purification. The resulting DNA fragment was ligated into BamHI-, BAP-dephosphorylated pSX20 and transformed into *E. coli* (FIG. 3). Clones carrying the PCR insert were completely resistant to Acc65I digestion. An *E. coli* host containing a pSX20-Acc65IM plasmid was made competent by CaCl₂ method.

The Acc65IR gene was amplified by PCR from genomic DNA. Following purification, the resulting PCR fragment was digested with XbaI+XmaI and ligated into XbaI-, XmaI-digested PRRS and transformed into *E. coli* host containing the pSX20-Acc65IM plasmid (FIG. 3).

EXAMPLE III

Production of Recombinant Acc65I Endonuclease 166 grams of *E. coli* cell pellet were suspended in 1 liter of Buffer A (20 mM Tris-HCl (pH 7.4), 10 mM 2-mercaptoethanol, 5% Gycerol) containing 200 mM NaCl, and passed through a Gaulin homogenizer at ~12,000 psig. The lysate was centrifuged at ~13,000×G for 40 minutes and the supernatant collected.

The supernatant solution was applied to a 372 ml Heparin Hyper-D column (Biosepra, Marlborough, Mass.) which had been equilibrated in Buffer A containing 200 mM NaCl. A 940 ml wash of buffer A containing 200 mM NaCl was applied, then a 2.2 L gradient of NaCl from 0.2M to 1M in buffer A was applied and fractions were collected. Fractions were assayed for Acc65I endonuclease activity by incubating with 1 microgram of pBC4 plasmid DNA (dam-, dcm-) (NEB#N0354S) in 50 microliters containing NEBuffer 3, supplemented with 100 μg/ml BSA for 5 minutes at 37° C. (NEB, Ipswich, Mass.). Acc65I activity eluted at 0.5M to 0.6M NaCl.

The Heparin Hyper-D column fractions containing the Acc65I activity were pooled and loaded directly onto a 63 ml Ceramic HTP column (Biosepra, Marlborough, Mass.) equilibrated in Buffer A containing 200 mM NaCl. A 160 mL wash of buffer A, containing 200 mM NaCl, was applied, then a 630 mL gradient of KHPO$_4$ (pH 7.0) from 0M to 0.55M in buffer A, containing 200 mM NaCl, was applied and fractions were collected. Fractions were assayed for Acc65I endonuclease activity by incubating with 1 microgram of pBC4 plasmid DNA (dam-, dcm-) (NEB#N0354S, NEB, Ipswich, Mass.) in 50 microliters NEBuffer 3, supplemented with 100 μg/ml BSA for 5 minutes at 37° C. Acc65I activity eluted at 0.2M to 0.3M KHPO4 (NEB, Ipswich, Mass.).

The Ceramic HTP column fractions containing the Acc65I activity were pooled and dialyzed into Buffer A, containing 200 mM NaCl (Biosepra, Marlborough, Mass.). This pool was loaded onto a 80 ml Q Sepharose column which had been equilibrated in buffer A containing 0.2M NaCl. A 130 mL wash of buffer A containing 200 mM NaCl was applied, then a 680 ml gradient of NaCl from 0.2M to 1M in buffer A was applied and fractions were collected. Fractions were assayed for Acc65I endonuclease activity by incubating with 1 microgram of pBC4 plasmid DNA (dam-, dcm-) (NEB#N0354S) in 50 microliters NEBuffer 3, supplemented with 100 μg/ml BSA for 5 minutes at 37° C. (NEB, Ipswich, Mass.). Acc65I activity eluted at 0.28M to 0.36M NaCl.

The Q Sephrarose column fractions containing the Acc65I activity were pooled and dialyzed into Buffer A, containing 200 mM NaCl. This pool was loaded onto a 21 ml Heparin TSK column which had been equilibrated in buffer A containing 0.2M NaCl. A 60 mL wash of buffer A containing 200 mM NaCl was applied, then a 200 ml gradient of NaCl from 0.2M to 1M in buffer A was applied and fractions were collected. Fractions were assayed for Acc65I endonuclease activity by incubating with 1 microgram of pBC4 plasmid DNA (dam-, dcm-) (NEB#N0354S) in 50 microliter NEBuffer 3 (NEB, Ipswich, Mass.), supplemented with 100 μg/ml BSA for 5 minutes at 37° C. Acc65I activity eluted at 0.4M to 0.48M NaCl.

The pool was dialyzed into Storage Buffer (10 mM KHPO4 pH 7.0, 100 mM NaCl, 11.0 mM DTT, 0.1 mM EDTA, 50% Gycerol). Eighty million units of Acc65I were obtained from this procedure. The Acc65I endonuclease thus produced was substantially pure and free of contaminating nucleases.

Activity Determination

Acc65I activity: Samples of 1 microliter were added to substrate solutions consisting of 1×NEBuffer 3 containing 1 microgram of pBC4 DNA (dam-, dcm-) (NEB#N0354S)/50 microliters, supplemented with 100 μg/ml BSA (NEB, Ipswich. MA). The reaction was incubated at 37° C. for 60 minutes. The reaction was terminated by adding 20 microliter of stop solution (50% glycerol, 50 mM EDTA pH 8.0, and 0.02% Bromophenol Blue (Sigma, St. Louis, Mo.) The reaction mixture was applied to a 1% agarose gel and electrophoresed. The bands obtained were identified by comparison with DNA size standards.

Unit Definition: One unit of Acc65I is defined as the amount of Acc65I required to completely cleave one microgram of pBC4 plasmid DNA in a reaction volume of 50 microliters of 1×NEBuffer 3 supplemented with 100 μg/ml BSA, within one hour at 37° C. (NEB, Ipswich, Mass.).

EXAMPLE IV

Expression of Acc65I Endonuclease in *E. coli*

The plasmid [pRRS-Acc65IR XbaI/XmaI] was transferred into *E. coli* containing compatible plasmid [pSX20-Acc65IM BamHI #4] and plated on Ap$^R$+Kn$^R$ plates at 37° C. overnight. Several individual colonies were inoculated into 50 ml LB+Ap$^R$+Kn$^R$ and grown at 37° C. overnight. All clones expressed Acc65I endonuclease activity at >10$^6$ μ/g per gram of wet *E. coli* cells.

What is claimed is:

1. An isolated DNA coding for a protein comprising SEQ ID NO: 5.

2. A cloning vector comprising the isolated DNA of claim 1.

3. A host cell transformed by the cloning vector of claim 2.

4. A method of producing recombinant Acc65I restriction endonuclease by culturing a host cell transformed with the vector in claim 2 under conditions suitable for expression of the restriction endonuclease.

* * * * *

SEQUENCE LISTING

```
<160> NUMBER OF SEQ ID NOS: 7

<210> SEQ ID NO 1
<211> LENGTH: 5812
<212> TYPE: DNA
<213> ORGANISM: unknown
<220> FEATURE:
<223> OTHER INFORMATION: Cloned DNA sequence from Acinetobacter
      calcoaceticus 65

<400> SEQUENCE: 1
gaattcaaaa ttggcgtaat tgtagcagat ttataaaggt tgttttcgca tgttagaaag      60
tgaaaatggt gttctagtat agatattatg aaaaagaaag agtcgtagtc cactctttct     120
ttctctatta attagttagc atttattaat cttttatccc aatcatcaat taatccaatt     180
ggtaaaccat taacacctga ggaactaaaa ctgattacct gaacatcttt agagtcaaga     240
tcaatatttg gtggaagatc attatcaacc aaaatcattt gacataaaat atttgcactt     300
ttgaattttt cagctaaatc aattaacgca ttaaataggt ttttatattt ttctggatca     360
gagacacctt cctcaacatc ttctctgttc tgattaaaat taggattttt ataagtttta     420
ccaagaaatt tacctaccgt atcgatcatt aataaacctg gtaaattcgt ctcttttgat     480
```

```
aattttttgct cggctttgtt gcacaaagat ttaaaaacta ggatttccca tatctactca    540
aatttaagtg acaactcggg tgtgaggtct gcctaaatcg gtaaatctat ttaatactgc    600
cactcgtgca tgaatctcat tgacttgact ttgaaagttt ctcgcactga gtttatcgcc    660
taataacttg atgcaatgca tcttggtttc aaccaaactt cgccgatgat agcctgacca    720
tttcttccaa atagttcttc ctaaacgctt aactgttcta agcaagtcat tgcgctatag    780
cgagcccatc tttttatctt tccatggctt ggcattttt ctgggggaa tcactgcatg     840 tgcttgccga tctgcaatga cctgacggca ttgttttgtg tcataagccc cgtcggtata    900
gactgaatca atctgctcat ccaacgggat ttgatcaagt aaatcaccaa gtacctgtga    960
atcacttaca ttgttggtcg tgagctgaac tgcccgtatt tgtagggttt tagcatctat   1020
accaatatgg agtttacgcc attggcgacg atattcaggc tgatgtttct tacgtttcca   1080
ttcaccttca cctaaaaact tcaagcccgt ggaatcgaca agtagatgca gtccattgca   1140
actcttctca tagctaattt gaatatcaat atgcttttgt cttctacaaa gcgtactgta   1200
atctggtgct gcccaattta atccgcaaag gttaatcaga ctttgaacaa aacctgtgac   1260
catgcgtaaa gacaatcgaa atagggattt gatcatcaga cagcactgga tggcagtatc   1320
agaataggtt tgatttcgac catgcttgcc ttgtgattgt gcgtaccact gggtctttgg   1380
atcgaaccaa atggcaatat cccacgatt aatgagagct cggttatatg cgggccaatt    1440
ggttgtgcgg tagattttgt gtgtaggctt cttcatttga aaattatatc gctgaagaag   1500
cccttaagaa tagctttgtg caacaaagcc gttttggatt aataaagtat ttcaaggtc    1560 aattataagg tcatagatta ttcaaagact tcaaatttaa attcatgatc tttatttta    1620 atatattcaa gtctagcaat cgaaacatca actattcttt tatatccagc ctcataggca   1680
acatgattag ttggtatttg gtctgaggat tccattaata tacattttcg atttgcacca   1740
ttcattttat ttaattcata aatggcgtgt gctgtagtag ctgaacctgc aaaaaaatct   1800
aaaactactg cattctcttc agacattgca tcaataattt ttttaataaa ttcaattggc   1860
tttggtgtat caaatatctt ttgaccaaaa atacttgtga tttcattagt tgctctttca   1920
gtataaagag acggatcatt ccatatagtt cgaatctttt tcctttttg accgtcctct   1980 ttcccagcat aattttttaac gtaaattacg ccattttac ttgaatataa ttgccataca   2040
cgttctctcg tagttgtttc tccccatagc catctacgat caattccttt cgaatccttt   2100
ggtaaaactt ttctccaacc ttcacgagga tcaaccgaaa cttcgcctgt ctcaagattt   2160
gcataaagtg gaaaggccat caaaggacgg tcgcttttca gactaccttc tcctttttt    2220 ctaaataacc catctatacg gtattttcca taagcatctg ctttatcata atcgtatct    2280 tcgtcagact ctcctcttaa ggtagcctga tttgatttac catatacaag taaatattca   2340
tgagtagatg ctaagttttt tttacttcct ttaccattct tggagcggca acaacaata    2400 ttgccaataa agtttttttc tccaaaaact ctatccatta ctattttaa atatggaaat   2460 tcataatcat caatactaac tgcaataact ccactgtcct ttaatagttc acgagctgtt   2520
actaaccgtg gaagcataaa ttcaacccat gcttcatgag atcccagtaa accgatttca   2580
ggcgattttc tattatcagg atagataaaa tttgatcctg tattataagg tggatctata   2640
taacacaaat caataatctc aggaccgttc aggagtaatt tccttaagga aattaagtta   2700
tctccactat aaataacagc atcagtttgc tcccaatttc ttgataaatt agaattagtt   2760
ttaacatcat tagttacaaa gtcaaaagag ctagcgtggg agaactcttg ttgtaactta   2820
cggattttag actcaattac tgatagcatg tcagctccta cttggaccaa cattataact   2880
```

```
gagcctgctc aagagaagga atgtaatgaa attaaatgct gagaatttaa gtattcagga    2940
acaattagca gaatttgatc aatggctcac agctagacta gataaaatca aagattcaga    3000
aaaattcaat tcagaaatta actccctctg taattgtatt accgtattat ctcctctttt    3060
agaaaacttc agtgatcctt ccacctgtac aattcatagc ttagtgaatg cggttataga    3120
agccagcaat agaatagtct ctggtagtag ttttggaggt gatgaagctg ctctcaacaa    3180
cttttatgag tcttttttta acttgctatt cctaaccagt ggggcaacag ataacaacct    3240
aaagaatcat tttctaatta aacttaatga agacgatatt acacctctca tacctaaacg    3300
tggttcaata aagaaacaga tcacattcaa actttatgaa attcctacaa ctactaaatc    3360
tgactttatc gctcgtacct tagcaagttg ttttacagga actaaatatc ccctcctagt    3420
aaagacagaa ccatttttcg atcttgaaac atactttaaa attttttag aagaatacat     3480 taagcttatt cttgatgatg aagaagattt attacaactc tgggctatct gccactcatt    3540
tgttgaatta tccactaacc ctcatggttc caatttgggt aaatatttat taaattcttg    3600
tacgattttt aaagttagag gtagtgtatc agcatcaggt ggtcacgtta ctgaatctat    3660
acttagggaa aagttatcaa acatcgggtt aagagctgat attgattaca ataataatga    3720
tgtcaaaatt ggtgatgatg aaattattga agacggaaa agaaaaaaga aaactcgtgc     3780
gtatgacttt ataattcctt ataaaataga taactgggaa ccaaaaccta agctatttat    3840
ccaatcacaa ttttacgctg gggattctgg cagtgtatct cataaagtcg tagatcaaac    3900
tcaaagttca agagtattta cactaaccaa atatccgaat gctaaatttg ttgaatattt    3960
agatggtgct ggttactacg cttctttaag aggtgattta cagcacatgc tatctttcag    4020
caatacagaa tcttttttc aagtaaaaag tattcttttta cgtttaagac gtgaattcca    4080
aaagatcgat ttttttaacag ctattgaaat tcagcatgct gtactaatca gcaaatctcg   4140
gactcataaa gatctccaaa atcttcttat aaaagataac tattctatcc aagaaataga    4200
aagagctatt caaaccaatt tagaactagg tcttattact aaaaatgaat cagatgaaat    4260 tgtaataccct acagaacata tttgtatcgc ccggagactt ttaattttag atattgctgc    4320
aaactattca tgctctatta ctcaggcaga aaagtctagc caaaaatatt tattagtacc    4380
gggcaatggg gccaataaag gaattaagga gtcaagcta gctgagttag cttttgactt     4440
atgtaaagat attaatataa caccgactga atttattgaa gacatcgaat ggctcttaga    4500
tgagggagta attaaacgat tttagtatca atggctgagc aagagctcag ccatatttt     4560 catttaatct aagctaaaat atttattcat tattcttgtt ctcaataaaa tagcactatt    4620
agaaatttgg ttatttttat acggattaag caaaactcaa tattataaaa tcattaactt    4680
atttcccctc ataagccaat aatattattt taaatttcca tagaaaaatc tamaaataat    4740
gacataacct gtccatacat cactacatta tctactttat aaaacaagaa tatcaacttg    4800
ttaaatttag gggcagaaga gtgaaaggta taattcttga ttttttcaatt cagaccaata   4860 gtggaattat ttcaggggaa gatcaaaaac gctattcatt tataggtagc gaatggaagg    4920
aaagttctcc acctcaacgt ggtcttaaga tagactttga tcttgacaca acaggacaag    4980
caatcggtgt atatcaagca ctagataatt ctatcagatc aaacgctcac ataactaata    5040
gtaccgaaaa atcagaagaa gattataata tttttgattg gttttattaag tgtttaaaga   5100 attatgcaaa tttttaatggt cgtgctagac gtaaggaatt ctggttcttt tatctcgcat   5160
tagtaatttg caatattttt gcgatggtct tagatgcaat tttagaaact gaagttattt    5220
```

-continued

| | |
|---|---|
| tttatggaat agttacttta gcaactatta ttccttttct tgctgtttct gctcgccgac | 5280 |
| tacatgacat aggaaaatcg ggctggtggt atcttattag tctaactatt ataggtatta | 5340 |
| ttctactaat tatctggtgg gcaaaagaag gagaagcctt tagtaatcca tatggtgata | 5400 |
| tagcgaaata aaaaatagac cctctcaatc tgagagggtc tattttttaa tataaggact | 5460 |
| tattaaaata tattttaaag atcctgaata ataaatctaa tctcaactcg tcgattattt | 5520 |
| gctgcattcg gattatcttt atttaataat ctatcaggac cataacctac gactgaaatt | 5580 |
| ctttgaacca attcagaaga ctgaagctgg gtaaacaatg cttttctagc ttctcttgct | 5640 |
| ctgccagctg ataagtata attatcatca aatggtgaac acacttgaga aatatttgat | 5700 |
| ttaacaccat ttactggtgc tgcatctgtg tgtccttcaa tctgtatatt cagcaatcga | 5760 |
| ttatcaatca tatttttttg gattaatgga gccaaccttt ccttgaaagc tt | 5812 |

<210> SEQ ID NO 2
<211> LENGTH: 1296
<212> TYPE: DNA
<213> ORGANISM: unknown
<220> FEATURE:
<223> OTHER INFORMATION: DNA sequence of methylase gene of Acinetobacter
      calcoaceticus 65

<400> SEQUENCE: 2

| | |
|---|---|
| atgttggtcc aagtaggagc tgacatgcta tcagtaattg agtctaaaat ccgtaagtta | 60 |
| caacaagagt tctcccacgc tagctctttt gactttgtaa ctaatgatgt taaaactaat | 120 |
| tctaatttat caagaaattg ggagcaaact gatgctgtta tttatagtgg agataactta | 180 |
| atttccttaa ggaaattact cctgaacggt cctgagatta ttgatttgtg ttatatagat | 240 |
| ccaccttata atacaggatc aaattttatc tatcctgata atagaaaatc gcctgaaatc | 300 |
| ggtttactgg gatctcatga agcatgggtt gaatttatgc ttccacggtt agtaacagct | 360 |
| cgtgaactat taaaggacag tggagttatt gcagttagta ttgatgatta tgaatttcca | 420 |
| tatttaaaaa tagtaatgga tagagttttt ggagaaaaaa actttattgg caatattgtt | 480 |
| gtttgccgct ccaagaatgg taaaggaagt aaaaaaaact tagcatctac tcatgaatat | 540 |
| ttacttgtat atggtaaaatc aaatcaggct accttaagag gagagtctga cgaagatacg | 600 |
| atttatgata aagcagatgc ttatggaaaa taccgtatag atgggttatt tagaaaaaaa | 660 |
| ggagaaggta gtctgaaaag cgaccgtcct ttgatggcct ttccactttt tgcaaatctt | 720 |
| gagacaggcg aagtttcggt tgatcctcgt gaaggttgga gaaaagtttt accaaaggat | 780 |
| tcgaaaggaa ttgatcgtag atggctatgg ggagaaacaa ctacgagaga acgtgtatgg | 840 |
| caattatatt caagtaaaaa tggcgtaatt tacgttaaaa attatgctgg gaaagaggac | 900 |
| ggtcaaaaaa ggaaaaagat tcgaactata tggaatgatc cgtctcttta tactgaaaga | 960 |
| gcaactaatg aaatcacaag tattttttggt caaaagatat ttgatacacc aaagccaatt | 1020 |
| gaatttatta aaaaaattat tgatgcaatg tctgaagaga atgcagtagt tttagatttt | 1080 |
| tttgcaggtt cagctactac agcacacgcc atttatgaat taaataaaat gaatggtgca | 1140 |
| aatcgaaaat gtatattaat ggaatcctca gaccaaatac caactaatca tgttgcctat | 1200 |
| gaggctggat ataaaagaat agttgatgtt tcgattgcta gacttgaata tattaaaaat | 1260 |
| aaagatcatg aatttaaatt tgaagtcttt gaataa | 1296 |

<210> SEQ ID NO 3
<211> LENGTH: 1620
<212> TYPE: DNA

<213> ORGANISM: unknown
<220> FEATURE:
<223> OTHER INFORMATION: DNA sequence of the restriction enzyme gene of
      Acinetobacter calcoaceticus 65

<400> SEQUENCE: 3

```
atgaaattaa atgctgagaa tttaagtatt caggaacaat tagcagaatt tgatcaatgg      60
ctcacagcta gactagataa aatcaaagat tcagaaaaat tcaattcaga aattaactcc     120
ctctgtaatt gtattaccgt attatctcct cttttagaaa acttcagtga tccttccacc     180
tgtacaattc atagcttagt gaatgcggtt atagaagcca gcatagaat agtctctggt      240
agtagttttg gaggtgatga agctgctctc aacaactttt atgagtcttt ttttaacttg     300
ctattcctaa ccagtggggc aacagataac aacctaaaga tcatttttct aattaaactt     360
aatgaagacg atattacacc tctcatacct aaacgtggtt caataaagaa acagatcaca     420
ttcaaacttt atgaaattcc tacaactact aaatctgact ttatcgctcg taccttagca     480
agttgtttta caggaactaa atatcccctc ctagtaaaga cagaaccatt tttcgatctt     540
gaaacatact ttaaaatttt tttagaagaa tacattaagc ttattcttga tgatgaagaa     600
gatttattac aactctgggc tatctgccac tcatttgttg aattatccac taaccctcat     660
ggttccaatt tgggtaaata tttattaaat tcttgtacga ttttttaaagt tagaggtagt   720
gtatcagcat caggtggtca cgttactgaa tctatactta gggaaaagtt atcaaacatc     780
gggttaagag ctgatattga ttacaataat aatgatgtca aaattggtga tgatgaaatt     840
attgaagacg ggaaaagaaa aagaaaaact cgtgcgtatg actttataat tccttataaa     900
atagataact gggaaccaaa acctaagcta tttatccaat cacaattta cgctggggat    960
tctggcagtg tatctcataa agtcgtagat caaactcaaa gttcaagagt atttacacta    1020
accaaatatc cgaatgctaa atttgttgaa tatttagatg gtgctggtta ctacgcttct    1080
ttaagaggtg atttacagca catgctatct ttcagcaata cagaatcttt ttttcaagta    1140
aaaagtattc ttttacgttt aagacgtgaa ttccaaaaga tcgattttt aacagctatt    1200
gaaattcagc atgctgtact aatcagcaaa tctcggactc ataaagatct ccaaaatctt    1260
cttataaaag ataactattc tatccaagaa atagaaagag ctattcaaac caatttagaa    1320
ctaggtctta ttactaaaaa tgaatcagat gaaattgtaa tacctacaga acatatttgt    1380
atcgcccgga gacttttaat tttagatatt gctgcaaact attcatgctc tattactcag    1440
gcagaaaagt ctagccaaaa atatttatta gtaccgggca atggggccaa taaaggaatt    1500
aaggagtcta agctagctga gttagctttt gacttatgta agatattaa tataacaccg    1560
actgaattta ttgaagacat cgaatggctc ttagatgagg gagtaattaa acgattttag    1620
```

<210> SEQ ID NO 4
<211> LENGTH: 431
<212> TYPE: PRT
<213> ORGANISM: unknown
<220> FEATURE:
<223> OTHER INFORMATION: Predicted amino acid sequence of the Acc65I
      methyltransferase protein

<400> SEQUENCE: 4

Met Leu Val Gln Val Gly Ala Asp Met Leu Ser Val Ile Glu Ser Lys
1               5                   10                  15

Ile Arg Lys Leu Gln Gln Glu Phe Ser His Ala Ser Ser Phe Asp Phe
            20                  25                  30

Val Thr Asn Asp Val Lys Thr Asn Ser Asn Leu Ser Arg Asn Trp Glu

```
                35                  40                  45
Gln Thr Asp Ala Val Ile Tyr Ser Gly Asp Asn Leu Ile Ser Leu Arg
 50                  55                  60

Lys Leu Leu Asn Gly Pro Glu Ile Ile Asp Leu Cys Tyr Ile Asp
 65                  70                  75                  80

Pro Pro Tyr Asn Thr Gly Ser Asn Phe Ile Tyr Pro Asp Asn Arg Lys
                 85                  90                  95

Ser Pro Glu Ile Gly Leu Leu Gly Ser His Glu Ala Trp Val Glu Phe
                100                 105                 110

Met Leu Pro Arg Leu Val Thr Ala Arg Glu Leu Leu Lys Asp Ser Gly
            115                 120                 125

Val Ile Ala Val Ser Ile Asp Asp Tyr Glu Phe Pro Tyr Leu Lys Ile
130                 135                 140

Val Met Asp Arg Val Phe Gly Glu Lys Asn Phe Ile Gly Asn Ile Val
145                 150                 155                 160

Val Cys Arg Ser Lys Asn Gly Lys Gly Ser Lys Asn Leu Ala Ser
                165                 170                 175

Thr His Glu Tyr Leu Leu Val Tyr Gly Lys Ser Asn Gln Ala Thr Leu
            180                 185                 190

Arg Gly Glu Ser Asp Glu Asp Thr Ile Tyr Asp Lys Ala Asp Ala Tyr
            195                 200                 205

Gly Lys Tyr Arg Ile Asp Gly Leu Phe Arg Lys Lys Gly Glu Gly Ser
210                 215                 220

Leu Lys Ser Asp Arg Pro Leu Met Ala Phe Pro Leu Tyr Ala Asn Leu
225                 230                 235                 240

Glu Thr Gly Glu Val Ser Val Asp Pro Arg Glu Gly Trp Arg Lys Val
                245                 250                 255

Leu Pro Lys Asp Ser Lys Gly Ile Asp Arg Arg Trp Leu Trp Gly Glu
            260                 265                 270

Thr Thr Thr Arg Glu Arg Val Trp Gln Leu Tyr Ser Ser Lys Asn Gly
            275                 280                 285

Val Ile Tyr Val Lys Asn Tyr Ala Gly Lys Glu Asp Gly Gln Lys Arg
290                 295                 300

Lys Lys Ile Arg Thr Ile Trp Asn Asp Pro Ser Leu Tyr Thr Glu Arg
305                 310                 315                 320

Ala Thr Asn Glu Ile Thr Ser Ile Phe Gly Gln Lys Ile Phe Asp Thr
                325                 330                 335

Pro Lys Pro Ile Glu Phe Ile Lys Lys Ile Ile Asp Ala Met Ser Glu
            340                 345                 350

Glu Asn Ala Val Val Leu Asp Phe Phe Ala Gly Ser Ala Thr Thr Ala
            355                 360                 365

His Ala Ile Tyr Glu Leu Asn Lys Met Asn Gly Ala Asn Arg Lys Cys
    370                 375                 380

Ile Leu Met Glu Ser Ser Asp Gln Ile Pro Thr Asn His Val Ala Tyr
385                 390                 395                 400

Glu Ala Gly Tyr Lys Arg Ile Val Asp Val Ser Ile Ala Arg Leu Glu
                405                 410                 415

Tyr Ile Lys Asn Lys Asp His Glu Phe Lys Phe Glu Val Phe Glu
            420                 425                 430

<210> SEQ ID NO 5
<211> LENGTH: 539
<212> TYPE: PRT
<213> ORGANISM: unknown
```

<220> FEATURE:
<223> OTHER INFORMATION: Predicted amino acid sequences of the Acc65I restriction endonuclease protein

<400> SEQUENCE: 5

```
Met Lys Leu Asn Ala Glu Asn Leu Ser Ile Gln Glu Gln Leu Ala Glu
 1               5                  10                  15
Phe Asp Gln Trp Leu Thr Ala Arg Leu Asp Lys Ile Lys Asp Ser Glu
             20                  25                  30
Lys Phe Asn Ser Glu Ile Asn Ser Leu Cys Asn Cys Ile Thr Val Leu
         35                  40                  45
Ser Pro Leu Leu Glu Asn Phe Ser Asp Pro Ser Thr Cys Thr Ile His
     50                  55                  60
Ser Leu Val Asn Ala Val Ile Glu Ala Ser Asn Arg Ile Val Ser Gly
65                  70                  75                  80
Ser Ser Phe Gly Gly Asp Glu Ala Ala Leu Asn Asn Phe Tyr Glu Ser
             85                  90                  95
Phe Phe Asn Leu Leu Phe Leu Thr Ser Gly Ala Thr Asp Asn Asn Leu
            100                 105                 110
Lys Asn His Phe Leu Ile Lys Leu Asn Glu Asp Asp Ile Thr Pro Leu
        115                 120                 125
Ile Pro Lys Arg Gly Ser Ile Lys Lys Gln Ile Thr Phe Lys Leu Tyr
    130                 135                 140
Glu Ile Pro Thr Thr Thr Lys Ser Asp Phe Ile Ala Arg Thr Leu Ala
145                 150                 155                 160
Ser Cys Phe Thr Gly Thr Lys Tyr Pro Leu Leu Val Lys Thr Glu Pro
            165                 170                 175
Phe Phe Asp Leu Glu Thr Tyr Phe Lys Ile Phe Leu Glu Glu Tyr Ile
            180                 185                 190
Lys Leu Ile Leu Asp Asp Glu Asp Leu Leu Gln Leu Trp Ala Ile
        195                 200                 205
Cys His Ser Phe Val Glu Leu Ser Thr Asn Pro His Gly Ser Asn Leu
    210                 215                 220
Gly Lys Tyr Leu Leu Asn Ser Cys Thr Ile Phe Lys Val Arg Gly Ser
225                 230                 235                 240
Val Ser Ala Ser Gly Gly His Val Thr Glu Ser Ile Leu Arg Glu Lys
            245                 250                 255
Leu Ser Asn Ile Gly Leu Arg Ala Asp Ile Asp Tyr Asn Asn Asn Asp
        260                 265                 270
Val Lys Ile Gly Asp Asp Glu Ile Ile Glu Asp Gly Lys Arg Lys Lys
    275                 280                 285
Lys Thr Arg Ala Tyr Asp Phe Ile Ile Pro Tyr Lys Ile Asp Asn Trp
290                 295                 300
Glu Pro Lys Pro Lys Leu Phe Ile Gln Ser Gln Phe Tyr Ala Gly Asp
305                 310                 315                 320
Ser Gly Ser Val Ser His Lys Val Val Asp Gln Thr Gln Ser Ser Arg
            325                 330                 335
Val Phe Thr Leu Thr Lys Tyr Pro Asn Ala Lys Phe Val Glu Tyr Leu
            340                 345                 350
Asp Gly Ala Gly Tyr Tyr Ala Ser Leu Arg Gly Asp Leu Gln His Met
        355                 360                 365
Leu Ser Phe Ser Asn Thr Glu Ser Phe Phe Gln Val Lys Ser Ile Leu
    370                 375                 380
Leu Arg Leu Arg Arg Glu Phe Gln Lys Ile Asp Phe Leu Thr Ala Ile
```

-continued

```
                385                 390                 395                 400
   Glu Ile Gln His Ala Val Leu Ile Ser Lys Ser Arg Thr His Lys Asp
                    405                 410                 415

Leu Gln Asn Leu Leu Ile Lys Asp Asn Tyr Ser Ile Gln Glu Ile Glu
                420                 425                 430

Arg Ala Ile Gln Thr Asn Leu Glu Leu Gly Leu Ile Thr Lys Asn Glu
                    435                 440                 445

Ser Asp Glu Ile Val Ile Pro Thr Glu His Ile Cys Ile Ala Arg Arg
        450                 455                 460

Leu Leu Ile Leu Asp Ile Ala Ala Asn Tyr Ser Cys Ser Ile Thr Gln
   465                 470                 475                 480

Ala Glu Lys Ser Ser Gln Lys Tyr Leu Leu Val Pro Gly Asn Gly Ala
                    485                 490                 495

Asn Lys Gly Ile Lys Glu Ser Lys Leu Ala Glu Leu Ala Phe Asp Leu
                500                 505                 510

Cys Lys Asp Ile Asn Ile Thr Pro Thr Glu Phe Ile Glu Asp Ile Glu
                515                 520                 525

Trp Leu Leu Asp Glu Gly Val Ile Lys Arg Phe
                530                 535

<210> SEQ ID NO 6
<211> LENGTH: 10
<212> TYPE: DNA
<213> ORGANISM: unknown
<220> FEATURE:
<223> OTHER INFORMATION: The product of self-ligating blunt ends filled
      in from sticky ends created by Acc65I cleavage of DNA

<400> SEQUENCE: 6
ggtacgtacc                                                              10

<210> SEQ ID NO 7
<211> LENGTH: 11
<212> TYPE: PRT
<213> ORGANISM: unknown
<220> FEATURE:
<223> OTHER INFORMATION: amino acid sequence motif characteristic of
      beta-class of DNA-adenine methyltransferases

<400> SEQUENCE: 7

Val Leu Asp Phe Phe Ala Gly Ser Ala Thr Thr
1               5                   10
```